United States Patent [19]

Gutman

[11] 4,134,985
[45] Jan. 16, 1979

[54] 5-CYCLOPROPANE CARBOXYLATE OXADIAZOLES AS INSECTICIDES AND ACARICIDES

[75] Inventor: Arnold D. Gutman, Berkeley, Calif.

[73] Assignee: Stauffer Chemical Company, Westport, Conn.

[21] Appl. No.: 796,777

[22] Filed: May 13, 1977

[51] Int. Cl.² .................... A01N 9/22; C07D 271/06; A01N 9/28
[52] U.S. Cl. ................ 424/272; 260/307 G; 260/564 G
[58] Field of Search .................... 260/307 G; 424/272

[56] References Cited

U.S. PATENT DOCUMENTS 3,879,407  4/1975  Hagarty ..................... 260/302 D

FOREIGN PATENT DOCUMENTS 841727  1/1976  Belgium.

OTHER PUBLICATIONS

Ogawa et al. (I), C.A. 78, 72155n (1973).
Ogawa et al. (II), C.A. 78, 120257w (1973).

*Primary Examiner*—Raymond V. Rush
*Attorney, Agent, or Firm*—Edwin H. Baker

[57] ABSTRACT

Compounds of the formula

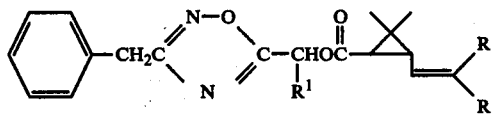

in which R is methyl or chlorine and $R^1$ is alkyl having 1 to 4 carbon atoms which are useful as insecticides and acaricides.

3 Claims, No Drawings

5-CYCLOPROPANE CARBOXYLATE OXADIAZOLES AS INSECTICIDES AND ACARICIDES

This invention relates to certain novel chemical compounds and their use as insecticides and acaricides. More particularly, this invention relates to certain novel 5-cyclopropane carboxylate oxadiazoles which are useful as insecticides and acaricides.

The compounds of the present invention that are useful as insecticides and acaricides are those having the structural formula

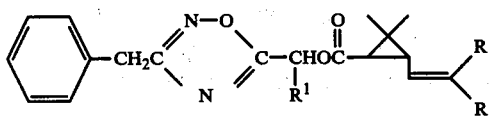

in which R is methyl or chlorine and $R^1$ is alkyl having 1 to 4 carbon atoms, preferably methyl.

The closest prior art is found in Belgium Pat. No. 841,727 and Japanese Pat. No. 4,734,358.

The compounds of this invention can be prepared according to the following reaction steps:

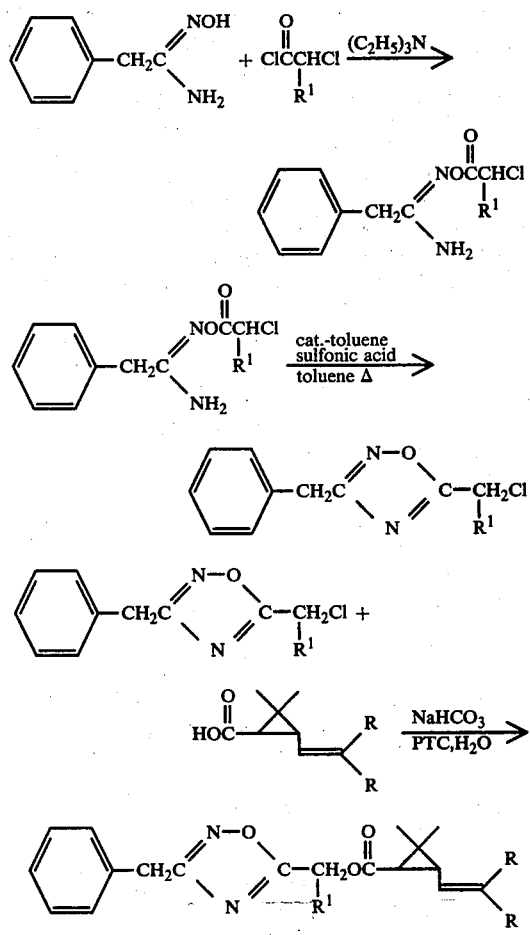

Preferably, reaction step 1 is carried out by slowly adding an equimole amount of the chloride reactant to a solution of the phenyl acetamide with stirring and cooling to around 0° C. An equimole amount of a hydrochloric acid acceptor such as triethyl amine is also used. The reaction is then continued for about 30 minutes with stirring at room temperature. After the reaction is complete, the salt is removed by filtration. Next, the solvent is removed and the reaction product of step 1 is dissolved in a solvent that is not miscible with water such as toluene.

Preferably, reaction step 2 is carried out by heating at reflux the aforesaid solution in the presence of an acid catalyst such as toluene sulfonic acid or napthalene sulfonic acid until all water is removed. The intermediate reaction product of step 2 is recovered and purified by standard procedures.

Preferably, reaction step 3 is carried out by refluxing a mixture of the reaction product of step 2 with equimole amounts of the carboxylic acid reactant and an inorganic base such as sodium bicarbonate or sodium carbonate along with a catalytic amount of a phase transfer catalyst (described hereinafter) in water. After heating at reflux for about two hours, the reaction mixture is cooled and the desired reaction product is recovered and purified by conventional techniques.

Phase transfer catalyst (PTC) used herein are known in the art and represent any catalyst which can effectively facilitate the transfer of ions or other reactive or functional chemical species or groups across the phase interface between one distinct liquid phase and a second distinct liquid phase, as in a heterogeneous system. In the majority of cases, one of the reactants is located in an aqueous phase and the other reactant in an organic phase.

Certain organic quarternary salts of Group VA of the Periodic Table of the Elements have been found effective as "phase transfer catalyst" useful in the present invention.

Examples of such catalysts are quarternary salts having the formula $$(R_3R_4R_5R_6M)^+ X^-$$

wherein $R_3$, $R_4$, $R_5$ and $R_6$ are hydrogen radicals having a total sum of 18 to 70 carbon atoms selected independently from the group consisting of alkyl, alkenyl, aryl, alkaryl, aralkyl and cycloalkyl radicals; M is a pentavalent ion selected from the group consisting of nitrogen, phosphorus, arsenic, antimony and bismuth, preferably nitrogen or phosphorus; and X is an anion which will dissociate from the cation in an aqueous environment, preferably a halide ion or a hydroxyl ion, most preferably chloride or bromide. The number of carbon atoms in the hydrocarbon substituents may vary considerably so as to contain from 1 to about 25 or more carbon atoms in each instance.

As used in the description of $R_3$, $R_4$, $R_5$ and $R_6$ above:

The term "alkyl" refers to a monovalent straight or branched chain saturated aliphatic hydrocarbon group of 1 to 25 carbon atoms, inclusive, e.g., methyl, ethyl, propyl, i-propyl, n-butyl, s-butyl, t-butyl, n-octyl, 2-methyloctyl, decyl, 6-methylundecyl, dodecyl and the like;

the term "alkenyl" refers to a monovalent straight or branched chain aliphatic hydrocarbon of 2 to 25 carbon atoms, inclusive, and containing at least one double bond, e.g., allyl, butenyl, butadienyl and the like;

the term "aryl" refers to a monovalent monocyclic or bicyclic aromatic hydrocarbon group, i.e., phenyl and naphthyl;

the term "alkaryl" refers to an aryl group as defined above, in which at least one hydrogen atom is substituted by an alkyl group as defined above, e.g., tolyl, xylyl, mesityl, ethylphenyl and the like;

the term "aralkyl" refers to an alkyl group as defined above, in which a hydrogen atom is substituted by an aryl or alkaryl group as defined above, e.g., benzyl, phenethyl, methylbenzyl, naphthylmethyl and the like; and the term "cycloalkyl" refers to a monovalent cyclical saturated hydrocarbon group of 4 to 8 carbon atoms, inclusive, i.e., cyclobutyl, cyclopentyl, cyclohexyl, cycloheptyl and cyclooctyl.

Mixtures of such quarternary salts may be likewise utilized in the practice of this invention. Double or multifunctional quarternary salts in which the general formula $(R_3R_4R_5R_6M)^+ X^-$ is repeated a plurality of times with the same or different substituent combinations can also be utilized effectively.

The preferred phase transfer catalysts are tetra-n-butyl phosphonium chloride, tri-n-butyl n-cetyl phosphonium bromide, hexadecyl tributyl phosphonium bromide, benzyl triethyl ammonium chloride, benzyl triethyl ammonium bromide, trioctyl ethyl ammonium bromide, tetraheptyl ammonium iodide, triphenyl decyl phosphonium iodide, tribenzyl decyl arsonium chloride, tetranonyl ammonium hydroxide, tricaprylyl methyl ammonium chloride and dimethyl dicoco ammonium chloride. The latter two catalysts are manufactured by General Mills Company, Chemical Division, Kankakee, Ill., and are alternatively designated by the names "Aliquat 336 ®" and "Aliquat 221 ®", respectively.

The term "catalytic amount" is used herein to represent any amount of phase transfer catalyst (quarternary salt) which will enhance the progress of the reaction. The amount of catalyst normally will range from about 0.05 weight percent to about 5.0 weight percent to about 1.0 weight percent based on the organic phase.

The terms catalytic activity and catalysis as they are herein used are intended to mean that a finite increase in the extent to which, or the rate at which, the reactants in the several phases react with each other is caused to occur by the presence in the system of the quarternary salt. Thus, there may or may not be an economic advantage to conducting the catalysis in the case of a particular reaction, but, as will be hereinafter shown in microencapsulation technology involving heterogeneous ionic reactions, a striking improvement in reactivity is realized which makes the heterogeneous or multiphase enviornment a much more attractive route by which to produce microcapsules than any method heretofore available.

EXAMPLE I

3-BENZYL-5-(1-CHLOROETHYL)1,2,4-OXADIAZOLE

This example teaches the synthesis of a representative intermediate of reaction steps 1 and 2.

First, 15.0 grams (0.1 mole) of phenyl acetamide oxime was combined with 100 milliliters of dry acetone in a 250 milliliter flask fitted with a thermometer and dropping funnel. The solution was stirred and cooled to 0° C. Next, 12.7 grams (0.1 mole) of 2-chloro propionyl chloride and 10.1 grams (0.1 mole) of triethyl amine was added. During the additions, the temperature was maintained at 0 to 5° C. After the additions were complete, the reaction mass was stirred at room temperature for 30 minutes and then was filtered free of salt. The filtrate was evaporated in vacuo at 50° and the residue was taken up in 300 milliliters of toluene. The toluene solution was charged to a 500 milliliter flask fitted with a Dean Stark water trap, 0.1 gram of toluene sulfonic acid was added, and the solution was heated under reflux until water ceased to be evolved. The toluene solution was then treated with activated carbon, filtered and evaporated in vacuo at 50° C. to yield 21.2 grams (95% of theory) of 3-benzyl-5-(1-chloroethyl)1,2,4-oxadiazole. $n_D^{30}$ 1.5040.

EXAMPLE II

3-BENZYL-5-{1-METHYL-1-[2,2-DIMETHYL-3-(2,2-DICHLOROVINYL) CYCLOPROPANE CARBOXYL]ETHYL}1,2,4-OXADIAZOLE

This example teaches the synthesis of a compound of this invention according to reaction step 3 using the intermediate of Example I.

First, 3.5 grams (0.016 mole) of the intermediate of Example I, 3.3. grams (0.016 mole) of the carboxylic acid reactant, 1.34 (0.016 mole) of sodium bicarbonate and 0.1 grams of a phase transfer catalyst, Aliquate 336, were combined with 100 milliliters of H$_2$O in a 200 milliliter round bottom flask. The mixture was stirred and heated under reflux for two hours. After cooling to room temperature, the mixture was poured into 200 milliliters of benzene and was washed with two 100 milliliter portions of H$_2$O. The benzene phase was then dried with MgSO$_4$ and evaporated in vacuo at 50° C. to yield 3.85 grams (60.9% of theory) of the desired product, 3-benzyl-5-{1-methyl-1-[2,2-dimethyl-3-(2,2-dichlorovinyl) cyclopropane carboxyl]ethyl}1,2,4-oxadiazole having a refractive index of $n_D^{30}$ 1.4960.

The following is a table of certain selected compounds that are preparable according to the procedure described hereto. Compound numbers are assigned to each compound and are used throughout the remainder of the specification.

TABLE I

| Compound Number | R | R$^1$ | $n_D^{30}$ |
|---|---|---|---|
| 1 | CH$_3$ | CH$_3$ | 1.4903 |
| 2$^a$ | Cl | CH$_3$ | 1.4960 |

$^a$Prepared in Example II

Insecticidal Evaluation Tests

The compounds of Table I were found to have insecticidal activity against the following insect species which were used in the evaluation tests described hereafter.

1. Housefly (HF) - *Musca domestica* (Linn.)
2. German Cockroach (GR) - *Blatella germanica* (Linn.)
3. Lygus Bug (LB) - *Lygus hesperus* (Knight)
4. Black Bean Aphid (BBA) - *Aphis fabae* (Scop.)
5. Green Peach Aphid (GPA) - *Myzus persicae* (Sulzer)
6. Cabbage Looper (CL) - *Trichoplusia ni* (Hubner)
7. Tobacco Budworm (TBW) - *Heliothis virescens* (F.)
8. Southern House Mosquito (MOS) - *Culex pipiens quinquefasciatus* (Say)

The insecticidal evaluation tests were conducted as follows:

Housefly: Test compounds were diluted in acetone and aliquots pipetted onto the bottom of 55 × 15 mm aluminum dishes. To insure even spreading of the chemical on the bottom of the dishes, 1 milliliter of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The $LD_{50}$ values are expressed below in Table II under the heading "HF", in terms of μg of the test compound per 25 female flies.

German Cockroach: Test compounds were diluted in a 50—50 acetone-water solution. Two cc of the solution were sprayed through a DeVilbiss type EGA hand spray gun into circular cardboard cages containing 10 one-month-old German cockroach nymphs. The test cages were covered on the bottom with cellophane and on the top with tulle netting. Percent mortality was recorded seven days later. Test concentrations ranged from 0.1% down to that at which approximately 50% mortality occurred. $LD_{50}$ values are expressed below in Table II under the heading "GR" in terms of percent of the test compound in the sprayed solution.

Lygus Bug: Test compounds were diluted in a 50—50 acetone-water solution. Two cc of the solution were sprayed through a DeVilbiss type EGA hand spray gun into circular cardboard cages containing one string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. $LD_{50}$ values are expressed below in Table II under the heading "LB" in terms of percent of the test compound in the sprayed solution.

Black Bean Aphid: Nasturtium plants (*Tropaeolum sp.*), approximately five cm tall, were transplanted into sandy loam soil in three-inch clay pots and infested with 25-50 black bean aphids of mixed ages. Twenty-four hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. $LD_{50}$ values are expressed below in Table II under the heading "BBA" in terms of percent of the test compound in the sprayed solution.

Green Peach Aphid: Radish plants (*Rhaphanus sativus*), approximately two cm tall, were transplanted into sandy loam soil in three-inch clay pots and infested with 25-50 green peach aphids of mixed ages. Twenty-four hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. $LD_{50}$ values are expressed below in Table II under the heading "GPA" in terms of percent of the test compound in the sprayed solution.

Cabbage Looper: Test compounds were diluted in a 50—50 acetone-water solution. Cotyledons of hyzini squash (*Calabacita abobrinha*), approximately 1 × 1.5 inches, were immersed in the test solutions for two-three seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. $LD_{50}$ values are expressed below in Table II under the heading "CL" in terms of percent of the test compound in the solution.

Tobacco Budworm: Test compounds were diluted in a 50—50 acetone-water solution. Sections of Romaine lettuce (*Latuca sativa*) leaves, approximately 1 × 1.5 inches, were immersed in the test solutions for two-three seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. $LD_{50}$ values are expressed below in Table II under the heading "TBW" in terms of percent of the test compound in the solution.

Southern House Mosquito Larvae (*Culex pipiens quinquefasciatus* Say): Insecticidal activity was determined using third instar larvae of the mosquito (*Culex pipiens quinquefasciatus*). Ten larvae were placed in a six ounce paper cup containing 100 milliliters of an aqueous solution of the test chemicals. The treated larvae were stored at 70° F. and 48 hours later the mortality was recorded. Test concentrations ranged from 1 ppm down to that at which approximately 50% mortality occurred. $LD_{50}$ values are expressed below in Table II under the heading "MOS" in terms of ppm of the test compound in the solution.

Acaricidal Evaluation Test

The two-spotted mite (2SM), *Tetranychus urticae* (Koch), was employed in tests for miticides. The test procedure was as follows:

Pinto bean plants (*Phaseolus sp.*) approximately 10 cm tall, were transplanted into sandy loam soil in three-inch clay pots and thoroughly infested with two-spotted mites of mixed ages and sexes. Twenty-four hours later, the infested plants were inverted and dipped for two-three seconds in 50—50 acetone-water solutions of the test chemicals. Treated plants were held in the greenhouse, and seven days later mortality was determined for both the adult mites and the nymphs hatching from eggs which were on the plants at the time of treatment. Test concentrations ranged from 0.05% down to that at which 50% mortality occurred. $LD_{50}$ values are expressed below in Table II under the headings "2SM-PE" (i.e., post-embryonic) and "2SM-Eggs", in terms of percent concentration of the test compound in the solution.

TABLE II

| Compound Number | HF (μg) | GR (%) | LB (%) | BBA (%) | CPA (%) |
|---|---|---|---|---|---|
| 1 | 24 | — | — | .008 | .01 |
| 2 | 5.6 | .02 | .03 | .0005 | .002 |

| Compound Number | CL (%) | TBW (%) | MOS (ppm) | 2SM-PE (%) | 2SM-EGGS (%) |
|---|---|---|---|---|---|
| 1 | .01 | — | .08 | — | — |
| 2 | .002 | .01 | .008 | .005 | .008 |

The compounds of this invention are generally formulated into a form suitable for convenient application. For example, the compounds can be prepared into a pesticidal composition in the form of emulsions, suspensions, solutions, dusts or aerosol sprays. In general, such pesticidal compositions will contain, in addition to the active compound, the inert adjuvants which are found normally in pesticide preparations. In these compositions, an active compound of this invention can be employed as the sole pesticide component or it can be used in an admixture with other compounds having similar utility.

The pesticide compositions of this invention can contain, (a) liquid adjuvants, such as organic solvents, sesame oil, xylene range solvents, heavy petroleum, etc.; water; (b) emulsifying agents; (c) surface active agents; (d) solid adjuvants such as talc; pyrophyllite, diatomite; gypsum; clays or (e) propellants, such as dichlorodifluoroemthane, etc.

If desired, however, the active compounds can be applied directly to feedstuffs, seeds, etc., or upon other materials upon which the pests feed. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active compound in the aforesaid compositions can vary within wide limits, ordinarily the active compound will comprise between about 1.0 and about 95% by weight of the pesticidal composition and more preferably between about 5% - 80% by weight.

I claim:

1. The compound of the formula

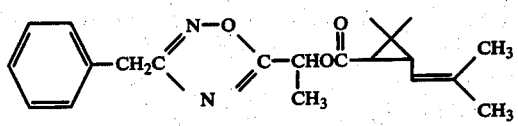

2. The pesticidal composition comprising a compound of the formula

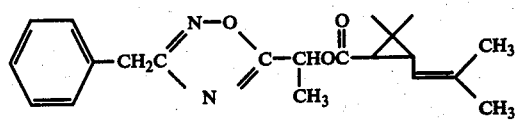

3. The method of controlling insects comprising applying to the habitat thereof an insecticidally effective amount of a compound of the formula

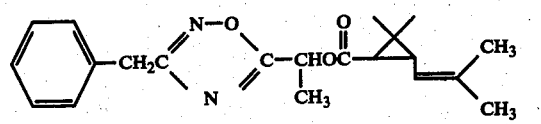

* * * * *